US007232690B1

(12) United States Patent
Lenz et al.

(10) Patent No.: US 7,232,690 B1
(45) Date of Patent: Jun. 19, 2007

(54) METHOD AND DEVICE FOR DETECTING AND ISOLATING PHARMACOLOGICAL COMPOUNDS BEING CONTAINED IN SUBSTANCE MIXTURES

(75) Inventors: Jana Lenz, Marburg (DE); Rudolf Matusch, Marburg (DE); Hans Rainer Hoffmann, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 303 days.

(21) Appl. No.: 10/088,868

(22) PCT Filed: Sep. 13, 2000

(86) PCT No.: PCT/EP00/08919

§ 371 (c)(1),
(2), (4) Date: Jun. 24, 2002

(87) PCT Pub. No.: WO01/22078

PCT Pub. Date: Mar. 29, 2001

(30) Foreign Application Priority Data

Sep. 22, 1999 (DE) ................................ 199 45 351

(51) Int. Cl.
*G01N 33/543* (2006.01)
(52) U.S. Cl. .................... 436/518; 422/68.1; 435/4; 435/6; 435/7.1; 435/7.92; 435/287.1; 435/287.3; 436/164; 436/172; 436/524; 436/532; 436/536; 436/538; 436/539; 436/540; 436/541
(58) Field of Classification Search .................. 435/4, 435/6, 7.1, 7.92, 287.1, 287.3; 436/164, 436/172, 518, 524, 532, 536, 538, 539, 540, 436/541; 422/68.1
See application file for complete search history.

(56) References Cited

U.S. PATENT DOCUMENTS

| 4,948,726 | A | * | 8/1990 | Longoria | ..................... | 435/7.5 |
| 5,300,490 | A | * | 4/1994 | Kunihiro et al. | ................ | 514/8 |
| 5,491,096 | A | | 2/1996 | Sportsman | | |
| 5,750,344 | A | | 5/1998 | Doyle | | |
| 5,824,503 | A | * | 10/1998 | Kurome et al. | ............ | 435/69.1 |
| 6,338,951 | B1 | * | 1/2002 | Soppet et al. | .............. | 435/69.1 |

FOREIGN PATENT DOCUMENTS

| EP | 0 819 930 A2 | 1/1998 |
| WO | 91/12331 | 8/1991 |
| WO | 92 02818 A | 2/1992 |
| WO | 99 02815 A | 2/1992 |
| WO | 92 17259 A | 10/1992 |
| WO | 93 20449 A | 10/1993 |
| WO | 97 01755 A | 1/1997 |
| WO | 99 33862 A | 7/1999 |

OTHER PUBLICATIONS onnerf jord p et al. : Journal of Chromatography a, N1 Elsevier Science, vol. 800, No. 2, Mar. 27, 1998 pp. 219-230, XP004113597.
Analytical Chemistry, vol. 69, No. 11, Jun. 1, 1997, pp. 2159-2164, "Pulsed Ultrafiltration Mass Spectrometry: A New Method for Screening Combinatorial Libraries", R. B. Van Breeman et al.
Analytical Chemistry, vol. 69, No. 9, May 1, 1997, pp. 1683-1691, "Immunoaffinity Ultrafiltration with Ion Spray HPLC/MS for Screening Small-Molecule Libraries", R. Wieboldt et al.
Proc. Natl. Acad. Sci., USA, vol. 89, May 1992, pp. 4505-4509, "Identification of highest-affinity ligands by affinity selection from equimolar peptide mixtures generated by robotic synthesis", R. N. Zuckermann et al.

* cited by examiner

*Primary Examiner*—Christopher L. Chin
(74) *Attorney, Agent, or Firm*—Birch, Stewart, Kolasch & Birch (57) ABSTRACT

A process for isolating and/or identifying at least one active chemical substance from a mixture of active and inactive chemical substances, is characterized by the steps:
  a) adding a target to said mixture and forming a complex of target and at least one active chemical substance of the mixture,
  b) separating the complex from the inactive chemical substances of the mixture, and
either
  c) liberating and isolating and/or identifying at least one active chemical substance from the separated complex
or
  d) identifying at least one active chemical substance of the mixture by subtracting from a chromatogram of the mixture of active and inactive chemical substances a chromatogram of the mixture of inactive chemical substances which is obtained after separation of the complex, and possibly liberating and isolating the at least one active substance from the separated complex.

21 Claims, 5 Drawing Sheets

METHOD AND DEVICE FOR DETECTING AND ISOLATING PHARMACOLOGICAL COMPOUNDS BEING CONTAINED IN SUBSTANCE MIXTURES

This application is the national phase under 35 U.S.C. § 371 of PCT International Application No. PCT/EP00/08919 which has an International filing date of Sep. 13, 2000, which designated the United States of America.

BACKGROUND OF THE INVENTION

1. Field of the Invention

Pharmacological research has developed—starting out from the use of exclusively natural sources, via the chemical synthesis of active substances and their testing by means of animal experiments—toward the targeted, computer-aided structure design of active substances using experimental and theoretical methods.

2. Description of the Related Art

With increased knowledge of the various causes of disease (e.g. lack or genetically caused alteration of a protein) pharmaceutical research and therapy by medicaments have become considerably more complex. Thus, over the past ten years, the genetic causes of some primarily neurodegenerative diseases such as Alzheimer's disease, Parkinson's disease, Huntington's disease, amyotrophic lateral sclerosis, prionic diseases and various ataxic syndroms could be elucidated by means of molecular-biological methods (Human Genome Project). This recognition of the biological changes underlying the diseases forms the basis for a shift from a symptomatic, palliative towards a causal therapy.

100 to 150 of the around 30.000 diseases described in medicine are relevant enough to be suitable as research projects for the pharmaceutical industry. The medicaments currently available aim at therapeutically influencing approx. 400 receptors, enzymes and other biomolecules. It is assumed, however, that approximately up to 10,000 genes and products thereof are suitable as targets for active agent research. Proving their pathological relevance requires, inter alia, molecular and cellular systems of informative value.

Apart from the rational design, which involves optimization of substance properties based on empirical values or based on known molecular structures, currently combinatorial chemistry and combinatorial biosynthesis, the latter being in the development stage, play an important part in drug research.

An important weak point of these methods is the limited diversity of synthetic substances compared to the structural complexity of vegetable and microbial secondary metabolites.

To be able to exploit this natural diversity, it is indispensable to create a tight link between classical natural product research, molecular medicine and organic chemistry. In the search for new lead structures, the selection of vegetable and animal organisms as well as fungi and microorganisms is performed according to the random principle, under chemotaxonomical aspects, on the basis of ecological observations and on the basis of ethnomedicinal previous knowledge.

Determining one or more active components from substance mixtures such as from substance libraries created by combinatorial chemistry or from natural product extracts, is, however, very labour-intensive.

Natural substance extracts, for example, generally consist of a large number (up to 2,000) of the most different substances spanning the entire polarity range, which is due to different basic structures and functional groups. As a rule, only relatively few compounds amount to already about 80% of the weight of the extract whereas the predominant part of the remaining compounds is present in low concentration down to the ppm region, i.e. non-equimolar. Frequently, however, only few substances, or even only one single substance, show the characteristic biological activity, and this activity may be caused by a substance which is present in the extract in traces.

Up to now, the processing and analysis of the mostly chromatographically separated components of a natural extract or of an extensive substance library generated by combinatorial chemistry has generally been performed using automated test systems with extremely high throughput (high-troughput screening; HTS). This method is, however, very labour- and cost-intensive. It is, for example, necessary to initially prepare from the natural product source (e.g. plant, animal, fungus, microorganism) selective extracts with solvents of increasing polarity and to subject these to biological tests. Further tests are made after subfractions have been formed from the respective effective selective extract.

Finally, an ultimate test is to show which pure substance(s), after isolation from the effective fraction, exhibit(s) biological activity and thus represents a "hit". The chromatographical separation in sublibraries and the testing thereof require several weeks each. To be able to recover sufficient amounts of the pure substance(s), it is therefore necessary to start with large quantities of extract. This, too, entails high costs for preparative HPLC columns and the high solvent requirement (both purchase and disposal).

Already by separating the subfractions, but all the more so by isolating the pure natural substances, possible synergistic or antagonizing effects of the individual components of the extract are lost in high-throughput screening. Thus, an extract which is effective in the first test may lose its biological action because the separation into individual substances prevents target-binding, which target-binding was possible only by the interaction of various components.

A process for determining effective components from a synthetic peptide library created by combinatorial chemistry and consisting of maximally 19 chemically very similar peptides which originate only from the replacement of amino acids and are present in equimolar amounts, is described by Zuckermann et al., Proc. Natl. Acad. Sci. USA 89, 4505-4509 (1992). To this end, an antibody was added in deficient quantity to such a peptide substance library, and the target(=anti-body)-peptide complex was separated by rapid gel filtration. The peptide was set free from the complex with 1% trifluoroacetic acid, and the structure was elucidated by mass spectroscopy and amino acid analysis. This process is, however, unsuitable for target-molecule complexes of smaller molecules (molecular weight below or equal 1500) since gel filtration technically works only with greater differences in molecular weight. Also, according to the authors, the process requires equimolar mixtures. Furthermore, the determination of synergistically active combinations of ligands is impossible or left to chance.

The experiments described by Wieboldt et al. in *Anal. Chem.*, 69, 1683-1691 (1997) are likewise directed to equimolar mixtures of 20 to 30, closely related molecules (synthetically produced derivatives having a general 1,4-benzodiazepine structure). The limited diversity of the synthetic substances does facilitate experimental processing, it is true, but at the same time represents a limiting factor for their use.

Likewise, the pulsed ultrafiltration mass spectrometry described by R. B. van Breemen et al. in *Anal. Chem.*, 69, 2159-2164 (1997) requires an equimolar substance library with 20 substances. Since release is accomplished only with organic solvents, covalently bonded substances can not be detected.

BRIEF SUMMARY OF THE INVENTION

It is therefore the object of the present invention to develop a method which can be carried out quickly and is efficient, for detecting and for isolating biologically, e.g. pharmacologically, active chemical substances and substance combi-nations, especially from non-equimolar mixtures such as natural substance extracts (e.g. from plants, animals, fungi, microorganisms).

This object is achieved by a process which is characterized by the following steps:
a) Adding a target to a mixture of chemical substances, e.g. an extract of a natural product,
b) forming at least one complex from the target and at least one active chemical substance, this chemical substance being bonded to the target;
c) separating the unbound chemical substance of the mixture from the at least one complex, and possibly analytic (e.g. chromatographic) detection thereof (=main experiment).

The substances which are to be determined in a separate experiment without target (blind test) and are present additionally or in higher concentrations, represent the sum of all substances bound by the target. These are isolated and their structure is elucidated.

As further steps for processing the complex the following may, however, also be suitable:
d) liberating the at least one active chemical substance bound to the target in the complex, with destruction of the bond between active chemical substance and the target in the complex,
e) separating the at least one liberated active chemical substance, and
f) identifying the at least one separated active chemical substance, and possibly comparing with the substances identified in step c.

DETAILED DESCRIPTION OF THE INVENTION

The term "biological target" refers to a protein (e.g. receptor, enzyme, antibody), a biological membrane or a whole (healthy or cancer) cell. Upon contact, especially when binding a matching active chemical substance to this target a reaction may be triggered that is characteristic for the target and is mostly connected with a biochemical process. In other words: The active chemical substance possesses a strong affinity to the specific target. Examples for such targets are the proteins thrombin, trypsin and the $\beta_2$-adrenoreceptor.

As "chemical substance" practically all those known from organic and natural product chemistry are suitable. Among these are low-molecular and high-molecular chemical substances, but not polymers of an unknown number of monomer units. Such chemically uniform substances of organic chemistry are known to those skilled in the art. Among these are aliphatic, aromatic and cyclic hydrocarbons and compounds with functional groups, such as carboxylic acids, alcohols, esters, aldehydes, lactones, amides, heterocycles, isoprenoids, terpenes, hydrocarbons, steroids, etc. Also, glycosides, peptides, proteins and enzymes can be taken into account as a suitable substance.

The molecular masses of suitable chemically uniform substances are generally above $M_r$=150. Thus, the known neutrotransmitters acetylcholine [$H_3CCO-O-CH_2-CH_2-N(CH_3)_3$]OH and nicotine have molecular masses of $M_r$=163 and $M_r$=162, respectively, and thus practically describe the lower limit of the molecular mass of the suitable chemical substances. The upper limit of the molecular mass is principally unlimited. Thus, high-molecular proteins ($M_r$ up to about 300,000) are definitely active chemically uniform substances of interest which can be separated from a mixture of different chemical substances by means of the process of the invention.

Non-uniform biopolymers such as glycogen, cellulose, etc., are unsuitable for the process of the invention since, due to their undefined number of monomer units, they do not represent chemically uniform substances for the purposes of the present invention.

Furthermore, with chemical substances a distinction must be made between active and inactive chemical substances. An active chemical substance is understood to be a substance which upon binding to a specific target is capable of triggering a reaction which is characteristic thereof. An active chemical substance is characterized by possessing an affinity to the target. An inactive chemical substance does not need to possess any affinity to the target.

A true upper limit of relative molecular mass of the suitable chemical sub-stances can thus not be indicated. Rather, it is only the simplicity of the processing which is determined substantially by the ratio of the relative molecular mass of the active chemical substance to the relative molecular mass of the target. The relative molecular mass of this target is generally very great, and can be, for example, above 1 million. As mentioned, the target may also be a whole cell. Chemical substances with small relative molecular mass (about 150 to about 30,000) can be easily separated from such targets on account of the great mass difference by conventional methods such as ultra-centrifugation. However, when the relative molecular mass of the active chemical substance and the relative molecular mass of the target are within comparable orders of magnitude, ultra-centrifugation only provides dissatisfactory separation results too, and more sophisticated or additional separating processes must be employed.

The term of "mixture of chemical substances" refers to a mixture of different chemical substances which contains at least one active chemical substance that fulfils the above-mentioned criterion, i.e. which upon contact is capable of triggering a reaction on a specific target. The mixture may also contain more than one of such active chemical substances. Furthermore, the mixture may also contain chemical substances which are not capable of triggering a reaction on a biological target. Generally, the inactive chemical substances account for the main portion in the mixture of different chemical substances. In particular, the inactive chemical substances contained in the chemical substance mixture are inactive only with respect to a specifically chosen target, but are quite capable of triggering such a reaction on another target.

In practice the mixture of chemical substances is preferably a substance library generated synthetically or using combinatorial chemistry, or an extract of a natural product. The term "extract of a natural product" in accordance with this definition is thus to be understood as meaning complex mixtures of chemically uniform substances originating from a biological source and preferably recovered from plants, parts of plants such as leaves, flowers, wood, roots, bark, etc., fungi, animals, glands, eggs and excrements of animals, microorganisms, etc. This is done using known methods, e.g. steam distillation, dry distillation, extraction with water, organic, inorganic or supercritical solvents; frequently also under simultaneous or subsequent chemical further processing such as esterification, saponification, salt formation, hydrogenation, dehydration, isomerization, alkylations, fermentation, enzymatic decomposition, etc. As regards the composition of their ingredients, the thus-obtained natural product extracts sometimes do no longer correspond to the composition present in the biological source. Generally, however, there is present a large number, i.e. at least 50, of the most different chemical substances; among these—as already mentioned—numerous substances are present only in traces, i.e. at a concentration of only some ppm. Frequently, however, in such an extract only a few or even only one single substance show the characteristic biological activity, this activity possible being due to a substance that is present in the extract only in traces. The mixture of chemical substances can also be a mixture of different natural product extracts. In the particular example, an extract of dandelion (taraxacum officinale) was chosen. Biological sources of particular importance are of course the medicinal plants, whose extracts have physiological and/or pharmacological effects and who are in part specified in the German pharmacopeia and the homeopathic pharmacopeia.

The "addition" of the target to the chemical substance mixture preferably takes place in solution, suspension or dispersion. In many cases, the addition takes place in an aqueous solution, especially in a solution the pH of which is stabilised with the aid of a suitable buffer. It is a particular advantage of the method described here that prior to adding the target, there is no previous separation of the mixture of chemical substances to a plurality of different fractions down to the pure chemical substances.

The term "complex" refers to a particle which can be isolated and which consists of the target to which at least one active chemical substance is bound. A target may also bind two or more active chemical substances. The two or more active chemical substances bound to the target in such a complex may be present in a certain, characteristic ratio to each other, which ratio with regard to the specific reaction of the special target corresponds to a synergistic effect. Those skilled in the art also speak of protein-ligand complexes since the constellation of a protein being chosen as the target is a frequent one.

In the complex, the at least one active chemical substance is "bound" to the target. Here, the type of bond between target and the active chemical substance(s) basically of no significance. Covalent or non-covalent bonds occur most frequently. The latter comprise, for example, hydrogen bridges, electrostatic interactions, e.g. between oppositely charged groups, metal complexing, interactions of lipophile groups of the active chemical substance with hydrophobic regions (so-called pockets) of the target, dipole-dipole interactions and cation-$\pi$ interactions. Also, it is often the combination of various interactions which causes the affinity of an active chemical substance to the target.

The "separation" of the at least one complex from the unbound, i.e. "free" inactive chemical substances of the mixture is basically performed utilizing common methods; with particular advantage such methods are being chosen which do not involve thermal loading of the complex. These are, for example, filtration, ultrafiltration, centrifugation, ultracentrifugation, equilibrium analysis, gel filtration or precipitation of the complex. Identification of the at least one "active" chemical substance bound to the target can sometimes be performed prior to liberating this chemical substance from the complex, e.g. time-of-flight mass spectroscopy (MALDI-TOF).

Filtration represents a particularly fast, simple and efficient separation method. It may be performed as ultrafiltration (e.g. utilizing Microcon filter units of the firm of Amicon) or with special filtration devices (e.g. Brandel cell collector).

The "liberation" of the at least one active chemical substance from the complex, however, facilitates its detection, isolation and especially its chemical characterisation. It follows the separation step after two or more wash procedures for removing unspecific adsorbed substances. Thereby, liberation of the bound active chemical substances from the complex is achieved. In this process, the bond existing in the complex between target and the at least one active chemical substance is broken once again. For this purpose, one uses physical or chemical methods—depending on the nature of the bond. This can be done, for example, by using an acid, aqueous-low-alkanolic solution, preferably with a mixture of trifluoroacetic acid/methanol/water, e.g. of a composition of 1/49,5/49,5 (Vol.-%).

The liberation step can be dispensed with if identification of the active chemical substance is not required, that is if the complex as such is to be identified. Liberation must be dispensed with if the active substance would be altered by the liberation conditions, or cannot be separated by the liberation solution. This is mainly the case in some covalent bonds. In these cases, identification of the active chemical substance is accomplished by means of the difference of the filtrates with target (=main experiment) and without target (blank sample). This procedure allows for all the chemical substances bound by the target to be detected simultaneously whereas liberation as a rule yields only few (e.g. one to three) active chemical substances; in addition, in the case of liberation, one can not be certain that the substances are unaltered.

The substances occurring additionally or in higher concentrations in the blind sample represent the potentially active chemical substances. They can be isolated, even in larger quantities, from the mixture of chemical substances (e.g. the natural product extract) by any separating method (e.g. chromatographic-ally).

"Separating" the at least one liberated active chemical substance from the target after destruction of the bond existing in the complex can be accomplished using the same, basically known methods that have already been mentioned. Here too, the simplest and most useful methods are utilized with preference, i.e. filtration and centrifugation. Separation of the active chemical substance(s) can also be accomplished by preparative HPLC.

"Identification" of the substances occurring in the blank sample in addition or in higher concentrations and of the at least one separated active chemical substance is performed by common methods such as HPLC, e.g conventional analytic HPLC, micro-HPLC, capillary HPLC or nano-HPLC, or by electro-chromatography, electrophoresis or coupling techniques of LC-MS or MS-MS. Identification of the active chemical substance(s) by means of the methods mentioned may, however, also be performed already before their liberation from the complex.

The process of the present invention is fundamentally different from the known high-throughput screening, mainly on account of the fact that by the targeted formation of complexes of target and at least one active chemical substance, and the subsequent separating of the unbound inactive chemical substance (main test), and the difference to the blank trial, it is possible, by means of this suitable specific target, to isolate and identify a single or a few active chemical substance(s) which bind to the corresponding protein (so-called "ligands") from a substance library or from a complex natural product mixture.

Instead of isolating each potentially interesting chemical substance individually, and supply it to the target, the latter is presented to the substance mixture. The complexes forming after recognition according to Emil Fischer's "Lock-and-key principle" are separated, e.g. by ultrafiltration, from the unbound low-molecular chemical substances, and are identified by comparative chromatography (target-free [=blind sample] versus target-containing [=main test] sample). To confirm the results, the ligands (the active chemical substances) are then additionally liberated—as far as they are stable and liberatable—from the complexes, identified by common methods, isolated, and structurally elucidated by common analytical methods.

The process according to the invention neither requires large amounts of proteins nor of extract, it requires small solvent volumes by downscaling to micromethods in analysis, requires no time-consuming subfractionating, and enables the discovery of synergistically active substance combinations. Radioactive and fluorescence marking can be dispensed with. The process of the invention naturally also enables the processing of larger quantities of extract, it being possible to "fish out" active chemical substances whose properties are not desired for the further use of the extract.

The process can be employed with particular advantage when from greater quantities of such extracts one intends to "fish out" only those active chemical substances which show interaction with the target concerned. The at least one separated active chemical substance may then be further used as active principle of a medicament instead of the natural product mixture. This is also of significance if more than one active chemical substance of the extract of natural product forms a complex with the target, and the relative ratio of the more than one active chemical substances to each other plays a dominant part with regard to the biological efficacy of the natural product extract (synergy effect).

An advantage of this process therefore also lies in the possibility of identifying active (synergistic) substance combinations, which are not detected in the high-throughput screening of individual substances.

Finally, it was also possible with the aid of this process to shift the recognition limit (detection limit) for active chemical substances against all expectations to the micromolar $K_i$-value region; i.e. the complexes of a target and an active chemical substance with a $K_i$-value of 1.7 µM were detectable.

The following examples serve to illustrate the process of the invention.

EXAMPLE 1

Isolation of a Thrombin-Inhibiting Substance of the 4-amidino-phenylalanine Type from a Randomly Selected Substance Library As a target, the serine protease thrombin was chosen. As substances of the substance library (the mixture of "inactive" chemical substances as defined above) the following five drugs were chosen, taking into account their water solubility, their absorption maxima and their chromatographic separability:

1. the centrally attacking $\alpha_2$-adrenoreceptor agonist clonidin-HCL

2. the mucolytic agent bromhexine-HCL 3. the tricyclic antidepressant amitryptiline-HCL 4. the neuroleptic of the phenothiazine type chlorpromazine-HCL 5. the neuroleptic of the phenothiazine type chlorprothixene-HCL.

As the thrombin inhibitor (the active chemical substance), the compound CRC 220 of Behringwerke (Marburg; $K_i$=2.5 nM) having the following structural formula was used:

The examined assays were of the following composition:

TABLE 1

| Sample | Blind Sample without Thrombin | Main experiment with Thrombin |
|---|---|---|
| Thrombin 2000 E/mg | 0 | 1 nmol 5 µmol/l |
| Clonidin-HCl | 2 nmol 10 µmol/l | 2 nmol 10 µmol/l |
| Bromhexine-HCl | 2 nmol 10 µmol/l | 2 nmol 10 µmol/l |
| Amitriptyline HCl | 2 nmol 10 µmol/l | 2 nmol 10 µmol/l |
| Chlorpromazine-HCl | 2 nmol 10 µmol/l | 2 nmol 10 µmol/l |
| Chlorprothixene-HCl | 2 nmol 10 µmol/l | 2 nmol 10 µmol/l |
| CRC 220 | 2 nmol 10 µmol/l | |
| 0.9% NaCl in water (purest) | ad 200 µl | ad 200 µl |

Incubation of the substance library and the inhibitor with thrombin took place at room temperature within 1 hour;

solvent: 0.9% of NaCl in $H_2O$. The separation of the protein-ligand complexes formed was accomplished by ultrafiltration (centrifugal). All filtration procedures and washes were carried out until dryness of the filters.

Filter: Microcon 10 (Amicon)

Centrifugation conditions: 9981×g, room temperature

Washing steps: 2×, each with 150 µl of 0.9% NaCl in $H_2O$, 4° C.

Ultrafiltration and analysis of the filtrate were followed by washing steps and the liberation of the ligand (the active chemical substance) from the protein-ligand complex retained on the filter by treatment with 200 µl of water/methanol/TFA (49.5/49.5/1) at room temperature.

The blind sample (without thrombin) was treated analogously in all steps so that a comparison of the filtrates was possible. The filtrates obtained in all steps were dried by means of a speed-VAC concentrator, and later dissolved in the corresponding HPLC flow agent of defined amount applying ultrasound and agitation.

Figure 2A:
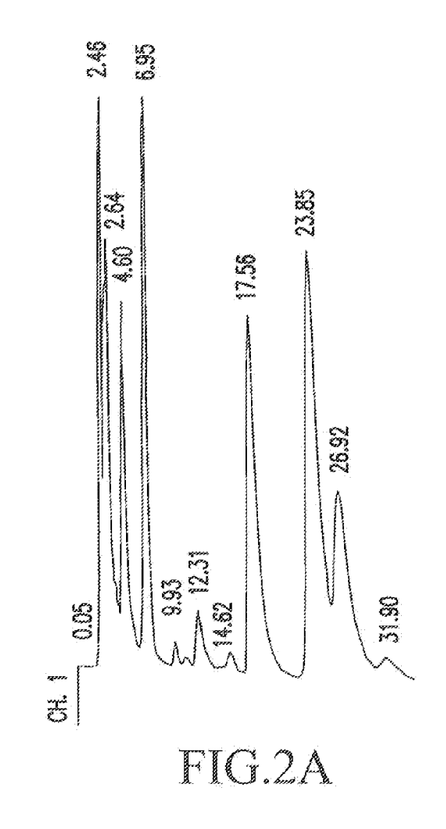
FIG. 2A shows a chromatogram of a mixture of chemical substances.
Figure 2B:
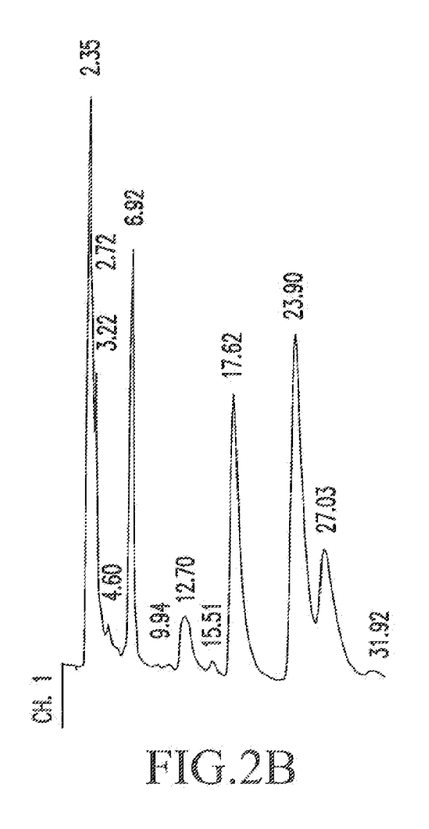
FIG. 2B shows a chromatogram of a filtrate without a target (blind sample).
Figure 2C:
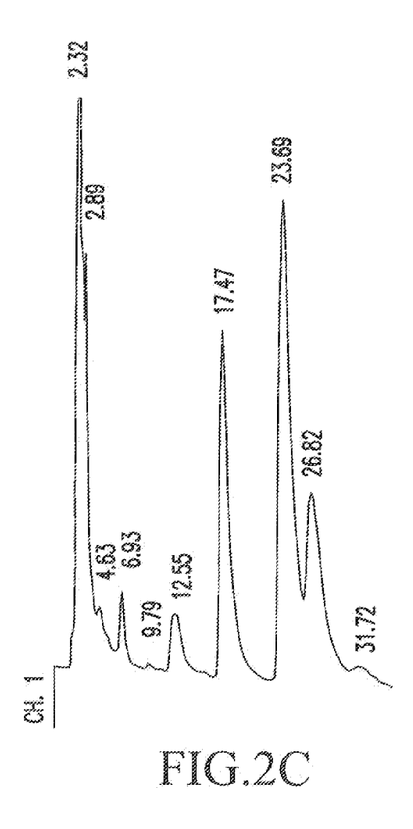
FIG. 2C shows a chromatogram of a filtrate with a thrombin target (test sample).

Identification of the ligands was accomplished by analytic HPLC: stationary phase Hypersil C 18 BDS, 3 µm, 150*0.3 mm, Fusica (LC Packings)—mobile phase: acetonitrile/water/TFA (35/65/0.01), isocratic, 5 µL/min, λ=230 mm. The results are shown in FIG. 2.

The difference between main experiment and blind sample is CRC 220 as active chemical compound. Since clonidin-HCL (4.6 min) occurs neither in the main test nor in the blind sample, it is not found by the target but by the filter. It is not an inhibitor.

EXAMPLE 2

Binding of Non-Equimolar Mixtures of amidinophenylalanines of Different Binding Strength to Trypsin The trypsin inhibitors of 3-amidinophenylalanine represented in the following by their structural formulae, were used as chemical substances, and the serine protease trypsin as target:

TABLE 3

| No. | Structure N/alpha/P2/ C alpha | Formula | $K_i$ [µmol/l] Thrombin | $K_i$ [µmol/l] Trypsin |
|---|---|---|---|---|
| 6 (120)*HCl | βNas/—/ Pzd-N-SMe |  | 0.0021 | 0.067 |
| 7 (105-95) *HCl | βNas/—/Ppd |  | 0.065 | 0.33 |
| 10 (110-79) *HCl | βNas/—/ iNip-Oet |  | 0.36 | 0.02 |

TABLE 3

Composition of the Assays

| Sample | Trypsin 10,600 E/mg | 6 ($K_i$ = 67 nM) | 7 ($K_i$ = 330 nM) | 10 ($K_i$ = 20 nM) | 0.9 NaCl in water (purest) |
|---|---|---|---|---|---|
| 261; 300 | 0 | 1.68 nmol 8.4 µmol/l | 8.25 nmol 41.25 µmol/l | 0.5 nmol 2.5 µmol/l | ad 200 µl |
| 262; 301; 302 | 10 nmol 50 µmol/l | 1.68 nmol 8.4 µmol/l | 8.25 nmol 41.25 µmol/l | 0.5 nmol 2.5 µmol/l | ad 200 µl |

The experiments were performed as described in Example 1.

TABLE 4

Results

| Sample | Substance | Filtrate [µmol/l] | 1st Wash [µmol/l] | 2nd Wash [µmol/l] | Liberation [µmol/l] |
|---|---|---|---|---|---|
| 261 | 6 | 7.44 | 0.71 | 0.05 | 0.01 |
|  | 7 | 31.57 | 3.13 | 0.26 | 0.13 |
|  | 10 | 0.05 | 0.02 | 0.0013 | 0.0011 |
| 262 | 6 | 0.67 | 0.23 | 0.15 | 6.09 |
|  | 7 | 22.22 | 3.68 | 1.29 | 8.49 |
|  | 10 | 0.02 | 0.0058 | 0.0012 | 0.53 |

EXAMPLE 3

Isolation and Identification of Natural Products of Extract of Taraxacum

Substance used for the assays:
a) extr. taraxaci spir. sicc. (natural product dry extract of the firm of Caelo)
Preparation of aqueous solutions:
suspension of the dry extracts in water (0.2 g in 20 ml)
5 min treatment in the ultrasound bath, allowed to stand for 30 min with occasional agitating
filtration through membrane filters (0.7 µm), subsequently through Anotop 25 filters (0.02 µm)
tannin test by means of $FeCl_3$, $Pb(CH_3COO)_4$ and gelatine: negative.
b) $\beta_2$-adrenoreceptor (=target)
Membrane preparation from Sf9 insect cells which had been infected for 3 days with a recombinant $\beta_2$-adrenergic-receptor-baculovirus (cells and viruses, plasmid construction, isolation of the recombinant baculovirus and preparation of the membrane: MPI für Biophysik, Molecular Membrane Biology Department, Frankfurt/Main, Dr. Helmut Reiländer) [H. Reiländer, *Febs letters*, 282, 441-444 (1991)]

In the assays, the extract of taraxacum and the membrane preparation were combined in different stoichiometric ratios, dissolved in 200 µl of binding buffer (150 mM of NaCl, 50 mM of tris, pH 8.2 in water).

The receptor-ligand binding was completed by 30-minute-long incubation of the mixture at 30-34° C. The solutions were then placed on a Microcon 10 centrifugal filter and centrifuged at 9981×g for 15 min or until dryness of the filter. The comparison of the chromatograms of the samples with (=main experiment) and without (=blind sample) receptor lead to identification of the bonded chemical substances. After two washing steps with binding buffer, the complexes present on the filter were separated by treatment with 200 µl of TFA (1/49.5/49.5).

TABLE 5

Composition of the assays:

| Sample | β2-Adrenergic Receptor (membrane preparation 10/98; 6.5 pmol of receptor per mg of protein | Extr. Taraxaci (10 mg/ml of aqueous extract, filtrated by Anotop 25 filter (Merck)) | Binding Buffer (150 mM NaCl; 50 mM of tris; pH 8.2) |
|---|---|---|---|
| 351 | 0 | 1.5 mg 7.5 g/l | ad 200 µl |
| 355 | 1.04 pmol 5.2 nmol/l | 1.5 pmol 7.5 nmol/l | ad 200 µl |
| 356 | 1.04 pmol 5.2 nmol/l | 1.5 pmol 7.5 nmol/l | ad 200 µl |
| 360 | 0 | 0.3 mg 1.5 g/l | ad 200 µl |
| 361 | 1.04 pmol 5.2 nmol/l | 0.3 mg 1.5 g/l | ad 200 µl |
| 362 | 0 | 0.6 mg 3 g/l | ad 200 µl |
| 363 | 1.04 pmol 5.2 nmol/l | 0.6 mg 3 g/l | ad 200 µl |
| 364 | 0 | 1.0 mg 5.0 g/l | ad 200 µl |
| 365 | 1.04 pmol 5.2 nmol/l | 1.0 mg 5.0 g/l | ad 200 µl |
| 366 | 1.04 pmol 5.2 nmol/l | 1.5 mg 7.5 g/l | ad 200 µl |
| 367 | 1.04 pmol 5.2 nmol/l | 1.5 mg 7.5 g/l | ad 200 µl |
| 369 | 1.04 pmol 5.2 nmol/l | 1.5 mg 7.5 g/l | ad 200 µl |
| 373 | 1.04 pmol 5.2 nmol/l | 1.5 mg 7.5 g/l | ad 200 µl |
| 374 | 0.52 pmol 2.6 nmol/l | 1.5 mg 7.5 g/l | ad 200 µl |
| 375 | 0.26 pmol 1.3 nmol/l | 1.5 mg 7.5 g/l | ad 200 µl |

The eluates from the following four filtration steps were centrifuged under vacuum until dryness, and the substances obtained were dissolved by means of ultrasound in 10 µl of the mobile phase of the HPLC (cf. Example 1), shortly before LC analysis.

TABLE 6

Results

| Sample | Substance | Filtrate [nmol/l] | 1st Wash [nmol/l] | 2nd Wash [nmol/l] | Liberation [nmol/l] |
|---|---|---|---|---|---|
| 351 | L3 | 740.3 | 51.0 | 8.0 | 11.9 |
|  | L6 | 5970.7 | 15045 | 750.8 | 195.0 |
|  | L7 | 3802.1 | 748.2 | 145.5 | 22.7 |

TABLE 6-continued

| | | Results | | | |
|---|---|---|---|---|---|
| Sample | Substance | Filtrate [nmol/l] | 1st Wash [nmol/l] | 2nd Wash [nmol/l] | Liberation [nmol/l] |
| 355 | L3 | 353.5 | 88.8 | 12.9 | 15.8 |
| | L6 | 1482.0 | 451.4 | 100.4 | 707.0 |
| | L7 | 1539.6 | 909.9 | 180.4 | 214.5 |
| 356 | L3 | 961.9 | 79.0 | 9.9 | 26.3 |
| | L6 | 1848.6 | 600.1 | 202.1 | 2199.1 |
| | L7 | 2183.1 | 1117.4 | 295.9 | 510.7 |
| 360 | L3 | 411.5 | 22.7 | 0 | 8.1 |
| | L6 | 2935.2 | 468.9 | 140.3 | 34.7 |
| | L7 | 1268.8 | 129.6 | 6.6 | 8.6 |
| 361 | L3 | 537.0 | 16.5 | 29.6 | 11.2 |
| | L6 | 1588.2 | 146.5 | 124.3 | 138.1 |
| | L7 | 1268.8 | 129.6 | 6.6 | 8.6 |
| 362 | L3 | 650.1 | 20.5 | 5.6 | 3.2 |
| | L6 | 3446.6 | 958.0 | 351.4 | 85.4 |
| | L7 | 1423.2 | 176.5 | 33.7 | 7.5 |
| 363 | L3 | 736.9 | 54.4 | 0 | 8.7 |
| | L6 | 1180.6 | 248.3 | 142.0 | 257.0 |
| | L7 | 1740.7 | 76.4 | 104.2 | 16.9 |
| 364 | L3 | 1034.4 | 36.9 | 3.0 | 5.3 |
| | L6 | 3752.4 | 1377.0 | 627.8 | 151.3 |
| | L7 | 1829.6 | 92.7 | 30.1 | 89.6 |
| 365 | L3 | 1221.4 | 51.7 | 8.6 | 9.8 |
| | L6 | 2291.6 | 626.7 | 141.6 | 439.6 |
| | L7 | 2746.8 | 74.0 | 11.2 | 111.9 |
| 366 | L3 | 2088.5 | 102.8 | 2.3 | 7.6 |
| | L6 | 5581.8 | 620.0 | 181.5 | 504.8 |
| | L7 | 4261.6 | 1425.3 | 213.1 | 168.2 |
| 367 | L3 | 2310.8 | 46.2 | 15.6 | 6.3 |
| | L6 | 5159.0 | 832.5 | 274.6 | 616.8 |
| | L7 | 6243.7 | 1509.0 | 199.2 | 232.9 |
| 369 | L3 | 2381.4 | 90.8 | 41.8 | 7.0 |
| | L6 | 7449.7 | 478.1 | 341.9 | 674.0 |
| | L7 | 3505.8 | 986.8 | 221.7 | 378.7 |
| 373 | L3 | 2450.0 | 91.7 | 26.6 | 36.2 |
| | L6 | 5562.6 | 182.7 | 277.1 | 2096.1 |
| | L7 | 4900.2 | 1176.5 | 285.4 | 847.8 |
| 374 | L3 | 2593.2 | 44.0 | 7.4 | 25.3 |
| | L6 | 8589.0 | 1062.4 | 476.6 | 1015.4 |
| | L7 | 5661.6 | 627.7 | 200.9 | 538.8 |
| 375 | L3 | 2252.1 | 39.7 | 19.6 | 19.0 |
| | L6 | 10838.5 | 921.1 | 433.9 | 279.9 |
| | L7 | 4921.4 | 631.3 | 112.3 | 154.4 |

The three "fished-out", i.e. obtained by complexation and subsequent liberation from the complex, ligands (L3=trans-caftarinic acid, L6=trans-chicorinic acid and L7=trans-diferoyl-tartaric acid ester) could be identified by means of UV, $^1$H-NMR and MS.

DESCRIPTION OF THE DRAWINGS

Figure 1:
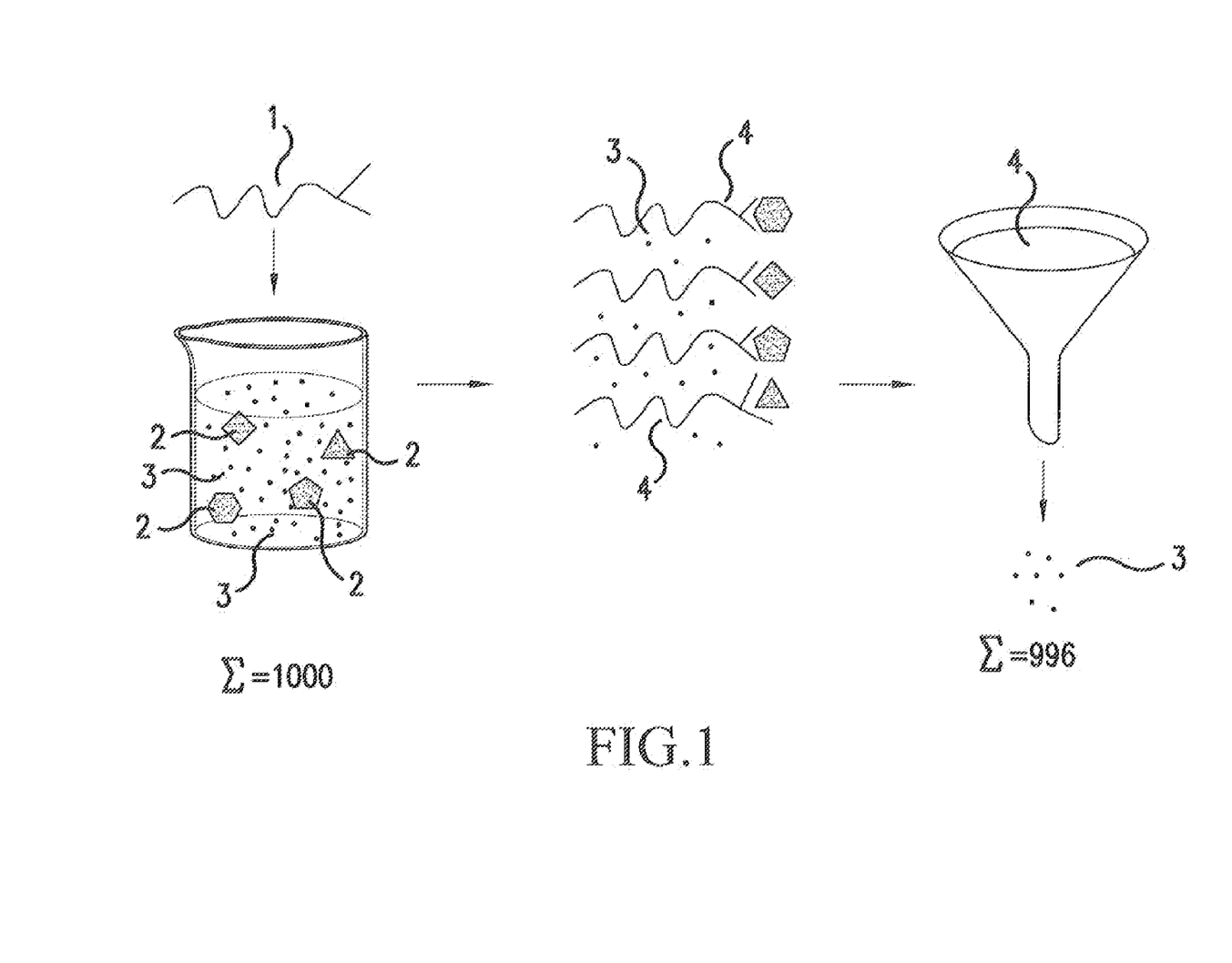
FIG. 1 shows a schematic representation of the formation of at least one complex of the target and active chemical substance and separation from inactive chemical substances.

FIG. 1 shows a symbolic representation of the formation of the at least one complex. To a mixture of 1000 different, non-equimolar chemically uniform substances (of which four are active) there is added a target. Four different complexes result, each of which containing one of the active chemical substances bound thereto. The 996 inactive substances can then be separated from the complex by means of ultrafiltration. The numbers mean:

1=target

2=various active chemical substances

3=various inactive chemical substances (dots)=

4=various complexes with at least one active chemical substance

FIG. 2 shows:
A) mixture of chemical substances with inhibitor CRC 220 clonidin-HCl (4.6 min), CRC 220 (6.9 min), bromhexine (12.3 min), amitryptiline (17.6 min), chlorpromazine-HCl (23.9 min), chlorprothixene-HCl (26.9 min)
B) filtrate without target [blind sample]
C) filtrate with target thrombin [main experiment]

Figure 3A:
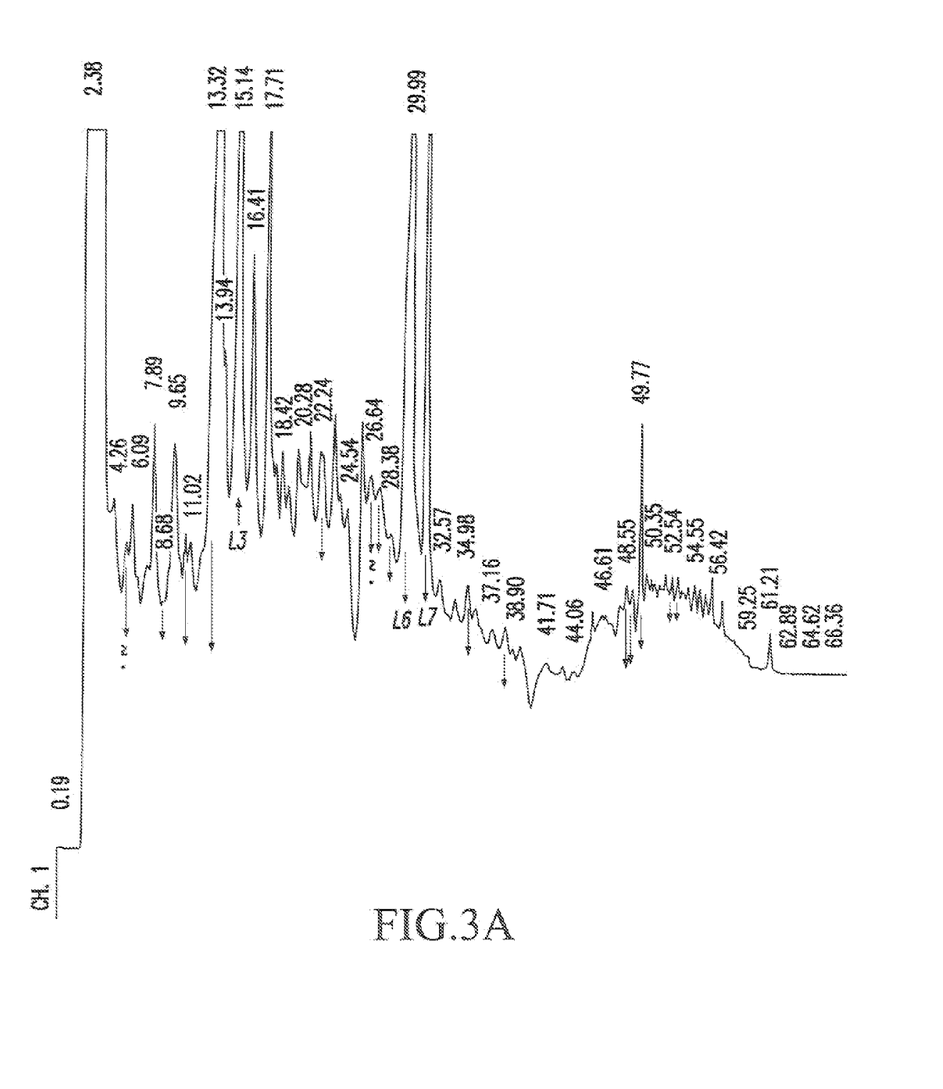
FIG. 3A shows a chromatogram of taraxacum (blind sample).
Figure 3B:
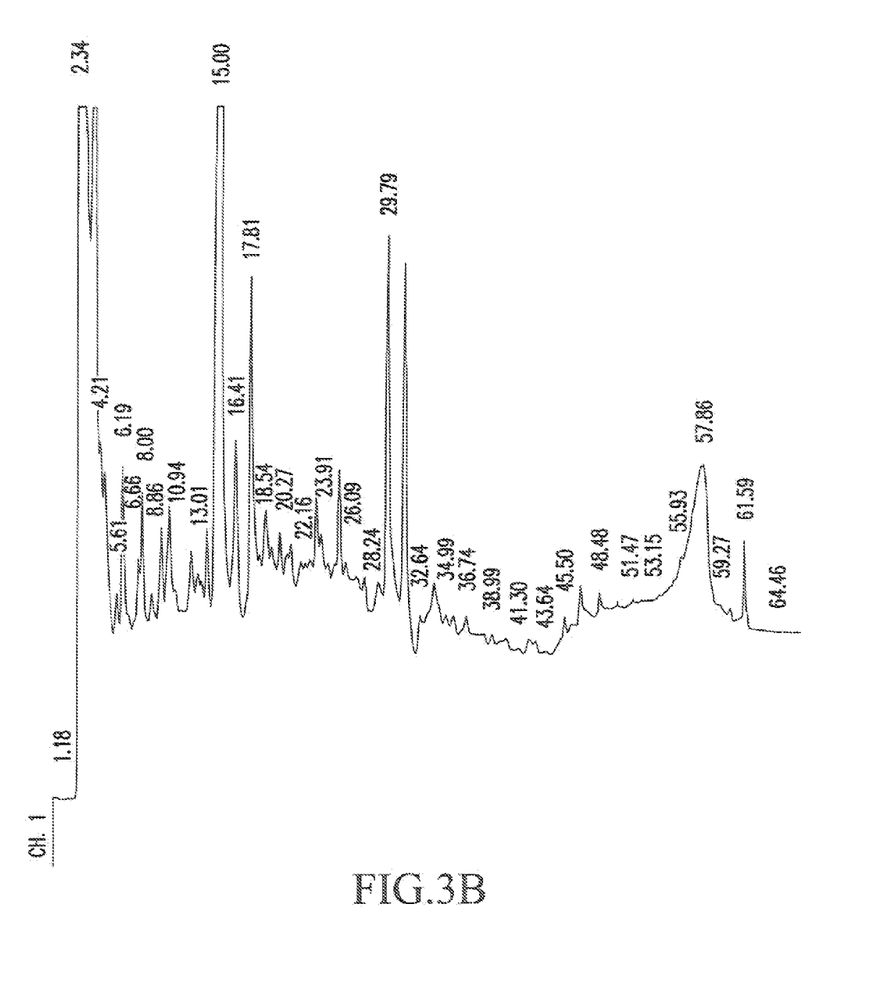
FIG. 3B shows a chromatogram of taraxacum (main experiment).
Figure 3C:
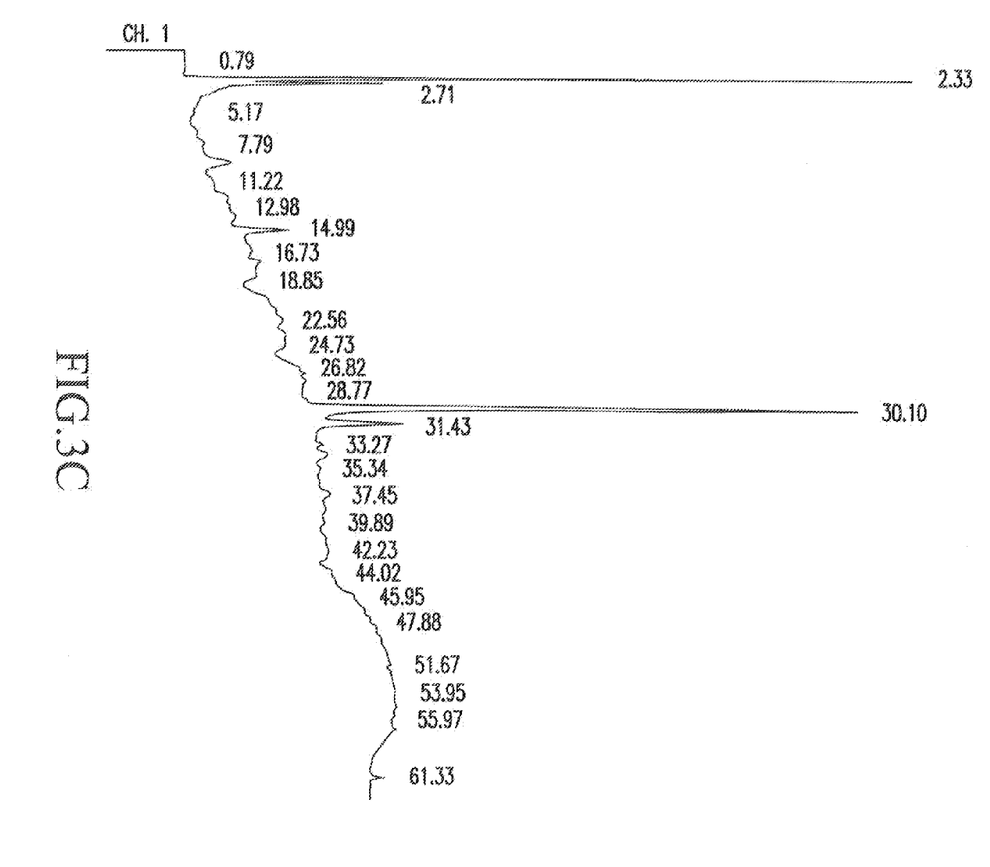
FIG. 3C shows a chromatogram of taraxacum liberation.

The chromatograms obtained in FIG. 3 show:

A) taraxacum (blind sample)

B) taraxacum (main experiment)

C) taraxacum liberation

The difference between blind sample and main experiment shows that approx. 12 substances are bound, whereas only 3 substances could be detected by the liberation method.

The invention claimed is:

1. A process for isolating and/or identifying at least one active chemical substance from a non-equimolar mixture of active or inactive chemical substances, comprising the steps:
   a) adding a target to said mixture and forming a complex comprising the target and at least one active chemical substance of the mixture;

b) separating the complex from the inactive chemical substances of the mixture by ultrafiltration or ultracentrifugation; and either c) liberating, isolating and identifying at least one active chemical substance from the separated complex; or d) identifying at least one active chemical substance of the mixture by subtracting from a chromatogram of the mixture of active and inactive chemical substances a chromatogram of the mixture of inactive chemical substances which is obtained after separation of the complex.

2. The process according to claim 1, wherein the adding of the target to said mixture is performed in a solution, a suspension or a dispersion.

3. The process according to claim 1, wherein the adding of the target to said mixture is performed in an aqueous solution.

4. The process according to claim 3, wherein a pH value of the aqueous solution is stabilized with the aid of a buffer.

5. The process according to claim 1, wherein said complex is created by a bond between the at least one active chemical substance and the target.

6. The process according to claim 1, wherein a bond between the target and the at least one active chemical substance is a covalent or non-covalent bond.

7. The process according to claim 1, wherein a non-covalent bond between the target and the at least one active chemical substance is formed by hydrogen bridges, electrostatic interaction, metal complexation, interaction of lipophile groups of the active chemical substance with the target, dipole-dipole interactions, or cation-$\pi$ interactions.

8. The process according to claim 1, wherein said isolating and/or identifying of the at least one active chemical substance of the separated complex is accomplished by at least one method selected from the group consisting of HPLC, electro-chromatography, electrophoresis and coupling techniques.

9. The process according to claim 8, wherein said coupling techniques are LCMS or MS-MS.

10. The process according to claim 8, wherein said method is microcapillary or nano-HPLC.

11. The process according to claim 1, wherein said identifying of the at least one active chemical substance of the mixture is accomplished by at least one method selected from the group consisting of HPLC, electro-chromatography, electrophoresis and coupling techniques.

12. The process according to claim 11, wherein said coupling techniques are LCMS or MS-MS.

13. The process according to claim 11, wherein said method is microcapillary or nano-HPLC.

14. The process according to claim 1, wherein said mixture is a substance library obtained from synthetic or combinatorial chemistry, or an extract of a natural product.

15. The process according to claim 1, wherein said mixture is a chemically modified extract of a natural product.

16. The process according to claim 1, wherein said mixture is a mixture of various natural product extracts.

17. The process according to claim 1, wherein said mixture contains at least 50 different chemical substances.

18. The process according to claim 1, wherein the target is a protein.

19. The process according to claim 1, wherein the target is an enzyme, a receptor, an antibody, a biological membrane or a cell.

20. The process according to claim 1, wherein the target is selected from the group consisting of thrombin, trypsin and $\beta$2-adrenoreceptor.

21. A process for isolating and/or identifying at least one active chemical substance from a non-equimolar mixture of active or inactive chemical substances, comprising the steps:

a) adding a target to said mixture and forming a complex comprising the target and at least one active chemical substance of the mixture;

b) separating the complex from the inactive chemical substances of the mixture by preparative HPLC, eletrochromatography or electrophoresis; and either c) liberating, isolating and identifying at least one active chemical substance from the separated complex; or d) identifying at least one active chemical substance of the mixture by subtracting from a chromatogram of the mixture of active and inactive chemical substances a chromatogram of the mixture of inactive chemical substances which is obtained after separation of the complex.

* * * * *